United States Patent
Faries, Jr. et al.

(10) Patent No.: US 7,350,373 B1
(45) Date of Patent: Apr. 1, 2008

(54) SURGICAL DISK DRAPE AND METHOD OF DISLODGING SURGICAL SLUSH WITHIN THERMAL TREATMENT SYSTEM BASINS

(75) Inventors: Durward I. Faries, Jr., Las Vegas, NV (US); Bruce R. Heymann, Vienna, VA (US); David Hendrix, Ashburn, VA (US)

(73) Assignee: O.R. Solutions, Inc., Chantilly, VA (US)

( * ) Notice: Subject to any disclaimer, the term of this patent is extended or adjusted under 35 U.S.C. 154(b) by 310 days.

(21) Appl. No.: 11/019,120

(22) Filed: Dec. 22, 2004

Related U.S. Application Data

(60) Provisional application No. 60/531,616, filed on Dec. 23, 2003.

(51) Int. Cl.
*A61B 19/02* (2006.01)
(52) U.S. Cl. .......................... 62/342; 128/849
(58) Field of Classification Search .......... 62/342–343; 128/849–856
See application file for complete search history.

(56) References Cited

U.S. PATENT DOCUMENTS

| | | |
|---|---|---|
| 2,613,511 A | 10/1952 | Walsh |
| 2,813,450 A | 11/1957 | Dzus |
| 3,519,979 A | 7/1970 | Bodenstein |
| 3,869,596 A | 3/1975 | Howie |
| 3,902,484 A | 9/1975 | Winters |
| 4,242,932 A | 1/1981 | Barmore |
| 4,270,067 A | 5/1981 | Thomas et al. |
| 4,284,880 A | 8/1981 | Keiser |
| 4,393,659 A | 7/1983 | Keyes et al. |
| 4,458,139 A | 7/1984 | McClean |
| 4,474,016 A | 10/1984 | Winchell |
| 4,522,041 A | 6/1985 | Menzel |
| 4,569,259 A | 2/1986 | Rubin et al. |
| 4,625,098 A | 11/1986 | Joe |
| 4,782,835 A | 11/1988 | Bernardini |
| 4,828,876 A | 5/1989 | Ohhara et al. |
| 4,869,271 A | 9/1989 | Idris |
| 4,903,710 A | 2/1990 | Jessamine et al. |
| 4,934,152 A | 6/1990 | Templeton |
| 4,953,269 A | 9/1990 | Ragsdale |
| 4,967,061 A | 10/1990 | Weber, Jr. et al. |
| 5,040,699 A | 8/1991 | Gangemi |
| 5,042,455 A | 8/1991 | Yue et al. |
| 5,042,981 A | 8/1991 | Gross |

(Continued)

FOREIGN PATENT DOCUMENTS

| | | |
|---|---|---|
| JP | 61-185967 | 11/1986 |

(Continued)

*Primary Examiner*—William E. Tapolcai
(74) *Attorney, Agent, or Firm*—Edell, Shapiro & Finnan, LLC

(57) ABSTRACT

A surgical drape according to the present invention includes a disk member for removable attachment to a thermal treatment system dislodgment mechanism. The mechanism manipulates the drape to dislodge congealed sterile liquid adhered to the sides of a container formed by the drape within a thermal treatment system basin. The disk member includes a base and a cover, where the cover is disposed on the top portion or sterile surface of the drape. The drape sterile surface may further include other disk member components (e.g., base, etc.). In addition, the drape may further include one or more sensors to detect conditions within the drape container.

24 Claims, 6 Drawing Sheets

U.S. PATENT DOCUMENTS

| | | |
|---|---|---|
| 5,129,033 A | 7/1992 | Ferrara et al. |
| 5,163,299 A | 11/1992 | Faries, Jr. et al. |
| 5,174,306 A | 12/1992 | Marshall |
| 5,310,524 A | 5/1994 | Campbell et al. |
| 5,331,820 A | 7/1994 | Faries, Jr. et al. |
| 5,333,326 A | 8/1994 | Faries, Jr. et al. |
| 5,345,063 A | 9/1994 | Reusche et al. |
| 5,363,746 A | 11/1994 | Gordon |
| 5,374,813 A | 12/1994 | Shipp |
| 5,383,476 A | 1/1995 | Peimer et al. |
| 5,386,835 A | 2/1995 | Elphick et al. |
| 5,396,905 A | 3/1995 | Newman et al. |
| 5,400,267 A | 3/1995 | Denen et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,435,322 A | 7/1995 | Marshall |
| 5,443,082 A | 8/1995 | Mewburn |
| 5,449,892 A | 9/1995 | Yamada |
| 5,457,962 A | 10/1995 | Faries, Jr. et al. |
| 5,463,213 A | 10/1995 | Honda |
| 5,502,980 A | 4/1996 | Faries, Jr. et al. |
| 5,522,095 A | 6/1996 | Faries, Jr. et al. |
| 5,524,478 A | 6/1996 | Joy et al. |
| 5,524,643 A | 6/1996 | Faries, Jr. et al. |
| 5,531,697 A | 7/1996 | Olsen |
| 5,539,185 A | 7/1996 | Polster |
| 5,551,240 A | 9/1996 | Faries, Jr. et al. |
| 5,615,423 A | 4/1997 | Faries, Jr. et al. |
| 5,653,938 A | 8/1997 | Faries, Jr. et al. |
| 5,658,478 A | 8/1997 | Roeschel et al. |
| 5,664,582 A | 9/1997 | Szymaitiz |
| 5,666,831 A | 9/1997 | Doros |
| 5,717,188 A | 2/1998 | Vaillancourt |
| 5,800,352 A | 9/1998 | Ferre et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,913,650 A | 6/1999 | Daoud |
| 5,950,438 A | 9/1999 | Faries, Jr. et al. |
| 6,003,328 A | 12/1999 | Faries, Jr. et al. |
| 6,035,855 A | 3/2000 | Faries, Jr. et al. |
| 6,077,267 A | 6/2000 | Huene |
| 6,087,636 A | 7/2000 | Faries, Jr. et al. |
| 6,091,058 A | 7/2000 | Faries, Jr. et al. |
| 6,102,044 A | 8/2000 | Naidyhorski |
| 6,255,627 B1 | 7/2001 | Faries, Jr. et al. |
| 6,371,121 B1 * | 4/2002 | Faries et al. ............... 128/849 |
| 6,810,881 B2 | 11/2004 | Faries, Jr. et al. |
| 6,860,271 B2 | 3/2005 | Faries, Jr. et al. |
| 6,910,485 B2 | 6/2005 | Faries, Jr. et al. |
| 6,918,395 B2 | 7/2005 | Faries, Jr. et al. |
| 7,041,941 B2 | 5/2006 | Faries, Jr. et al. |
| 7,176,030 B2 | 2/2007 | Faries, Jr. et al. |
| 2003/0231990 A1 | 12/2003 | Faries, Jr. et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Faries, Jr. et al. |
| 2005/0247169 A1 | 11/2005 | Faries, Jr. et al. |
| 2006/0065276 A1 | 3/2006 | Kammer et al. |
| 2006/0086361 A1 | 4/2006 | Kammer et al. |
| 2006/0091128 A1 | 5/2006 | Kammer et al. |
| 2006/0194324 A1 | 8/2006 | Faries, Jr. et al. |
| 2006/0260443 A1 | 11/2006 | Faries, Jr. et al. |
| 2007/0089753 A1 | 4/2007 | Faries, Jr. et al. |

FOREIGN PATENT DOCUMENTS

| | | |
|---|---|---|
| JP | 06-123532 | 5/1994 |

* cited by examiner

SURGICAL DISK DRAPE AND METHOD OF DISLODGING SURGICAL SLUSH WITHIN THERMAL TREATMENT SYSTEM BASINS

CROSS-REFERENCE TO RELATED APPLICATIONS

This application claims priority from U.S. Provisional Patent Application Ser. No. 60/531,616, entitled "Surgical Disk Drape and Method of Dislodging Surgical Slush Within Thermal Treatment System Basins" and filed Dec. 23, 2003. The disclosure of the above-mentioned provisional application is incorporated herein by reference in its entirety.

BACKGROUND OF THE INVENTION

1. Technical Field

The present invention pertains to surgical drapes for use with thermal treatment systems, such as the types of thermal treatment systems disclosed in: U.S. Pat. Nos. 4,393,659 (Keyes et al.), 4,934,152 (Templeton), 5,163,299 (Faries, Jr. et al.), 5,331,820 (Faries, Jr. et al.), 5,333,326 (Faries, Jr. et al.), 5,400,616 (Faries, Jr. et al.), 5,402,644 (Faries, Jr. et al.), 5,429,801 (Faries Jr. et al.), 5,457,962 (Faries, Jr. et al.), 5,502,980 (Faries, Jr. et al.), 5,522,095 (Faries, Jr. et al.), 5,524,643 (Faries, Jr. et al.), 5,551,240 (Faries, Jr. et al.), 5,615,423 (Faries, Jr. et al.), 5,653,938 (Faries, Jr. et al.), 5,809,788 (Faries, Jr. et al.), 5,816,252 (Faries, Jr. et al.), 5,857,467 (Faries, Jr. et al.), 5,862,672 (Faries, Jr. et al.), 5,879,621 (Faries, Jr. et al.), 5,950,438 (Faries, Jr. et al.), 6,003,328 (Faries, Jr. et al.), 6,035,855 (Faries, Jr. et al.), 6,087,636 (Faries, Jr. et al.), 6,091,058 (Faries, Jr. et al.), 6,255,627 (Faries, Jr. et al.), 6,371,121 (Faries, Jr. et al.) and 6,810,881 (Faries, Jr. et al.); and U.S. Patent Application Publication Nos. 2004/0200483 (Faries, Jr. et al.), 2004/0200480 (Faries, Jr. et al.), 2003/0231990 (Faries, Jr. et al.) and 2003/0172937 (Faries, Jr. et al.). The disclosures in the above-mentioned patents and patent application publications are incorporated herein by reference in their entireties.

2. Discussion of the Related Art

The above-referenced Keyes et al. patent (U.S. Pat. No. 4,393,659) discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent (U.S. Pat. No. 4,934,152), the Keyes et al. system has a number of disadvantages. In particular, the separate product basin must be removed and re-sterilized after each use. Additionally, the glycol or other thermal transfer medium is highly flammable or toxic and, in any event, complicates the procedure. The Templeton patent (U.S. Pat. No. 4,934,152) discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al. patent (U.S. Pat. No. 5,163,299) notes that scraping congealed liquid from the drape is undesirable in view of the potential for damage to the drape, resulting in a compromise of sterile conditions. As a solution to the problem, the Faries, Jr. et al. patent (U.S. Pat. No. 5,163,299) proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

Accordingly, several of the Faries, Jr. et al. patents (e.g., U.S. Pat. Nos. 5,331,820; 5,400,616; 5,457,962; 5,502,980; 5,653,938; 5,809,788; 5,857,467; 5,950,438; 6,003,328; and 6,035,855) resolve the problem of manual drape manipulation by disclosing various techniques and/or dislodgment mechanisms to automatically remove the congealed liquid adhering to the drape without endangering the integrity of the drape. For example, U.S. Pat. No. 5,331,820 addresses the problem of removing congealed frozen sterile medium from the sides of a sterile drape container in a surgical slush machine. Specifically, the sterile drape container is conformed to a cooled basin to establish a sterile field above the basin. The drape container collects a frozen sterile medium (e.g., saline) in a sterile slush-like consistency. The frozen medium tends to attach to the sides of the drape container in large clumps or pieces rather than automatically collecting within the container interior. The patent (U.S. Pat. No. 5,331,820) discloses a technique for automatically manipulating the drape relative to the basin wall to thereby cause the frozen congealed medium to detach from the drape sides and collect interiorly as the desired slush. Some of the embodiments disclosed in the patent (U.S. Pat. No. 5,331,820) cyclically move a plate or disk disposed between the drape and basin to manipulate the drape. The disk is described as being either secured to a movable machine or secured directly to the drape.

Since it has been found that, for many applications, it is more convenient to have the plate or disk secured directly to the drape, some of the aforementioned Faries, Jr. et al. patents (e.g., U.S. Pat. Nos. 5,457,962 and 5,502,980) disclose a disk or plate bonded to the underside of a sterile drape. The disk is provided with a fitting suitable for engaging a cyclically movable member to permit the disk to be cyclically moved in a manner to separate the drape container sides from the basin and cause frozen congealed pieces of sterile medium to fall into a slush pile.

In addition, when insignificant amounts of liquid are present within a thermal treatment system basin, the system cooling mechanism operates with minimal thermal resistance, thereby enabling the mechanism to become damaged. Further, the drapes employed by the system may be damaged by being disposed proximate the cooling mechanism without having the liquid to absorb the thermal energy. Since only sterile drapes are to be used during surgical procedures, a leak in a surgical drape compromises sterility and contaminates the entire surgical procedure, thereby increasing the risk of injury to a patient.

The related art has attempted to overcome this problem by employing sensing devices with surgical drapes. For example, U.S. Pat. No. 6,102,044 (Naidyhorski) discloses an electrode carrying surgical drape including a polymeric film having opposing surfaces and an electrode receiving aperture therethrough. An electrode is disposed through the aperture, while patches sealingly affix electrode portions to each of the opposing surfaces of the polymeric film in the vicinity of the aperture to form a reinforced laminated structure capable of maintaining the sterility of an established sterile field.

U.S. Pat. No. 6,810,881 (Faries, Jr. et al.) discloses a drape including a sensing device and disposed over a thermal treatment system having a basin recessed therein to form a drape container or receptacle within the basin for collecting a sterile medium. The thermal treatment system may either heat or congeal the sterile medium. The sensing device is typically disposed through the drape to provide a signal indicating the presence of liquid and/or leaks within the drape container to the system to facilitate control of system operation. In addition, the sensing device may be affixed to a plural basin drape utilized for a multiple basin thermal treatment system. The drape forms a drape receptacle within each basin, while a sensing device is typically disposed within each drape receptacle to detect the presence of liquid and/or a leak within that drape receptacle to facilitate control of system operation in substantially the same manner described above.

The above-described drapes can stand some improvement. In particular, the disk drape of the Faries, Jr. et al. patents (e.g., U.S. Pat. Nos. 5,457,962 and 5,502,980) preferably employs the disk on the underside of the drape. This requires medical personnel to manipulate the disk through the drape from the top or sterile drape surface in order to position the disk on the dislodgment mechanism and maintain drape sterility, thereby complicating placement of the disk on the dislodgment mechanism. Further, the above-described sensor drapes tend to subject the sensor or electrodes to accidental damage during stirring of solution within the basin by medical personnel. Moreover, the sensors tend to provide false readings in response to conductive objects placed within the basin in contact with the sensors. In order to protect the sensor and/or insulate the sensor from objects placed in a basin, a protective sleeve is generally employed, thereby increasing drape materials and costs.

OBJECTS AND SUMMARY OF THE INVENTION

Accordingly, it is an object of the present invention to enable attachment of a drape to a dislodgment mechanism via a disk secured to a sterile drape side and manipulable by medical personnel.

It is another object of the present invention to protect a sensor of a thermal treatment system drape by utilizing a disk for engaging a thermal treatment system dislodgment mechanism to cover the sensor.

Yet another object of the present invention is to insulate a sensor of a thermal treatment system drape from conductive objects placed in a thermal treatment system basin by utilizing a disk for engaging a thermal treatment system dislodgment mechanism to cover and insulate the sensor.

The aforesaid objects may be achieved individually and/or in combination, and it is not intended that the present invention be construed as requiring two or more of the objects to be combined unless expressly required by the claims attached hereto.

According to the present invention, a surgical drape includes a disk member for removable attachment to a thermal treatment system dislodgment mechanism. The mechanism manipulates the drape to dislodge congealed sterile liquid adhered to the sides of a container formed by the drape within a thermal treatment system basin. The disk member includes a base and a cover, where the cover is disposed on the top portion or sterile surface of the drape. The drape sterile surface may further include other disk member components (e.g., base, etc.).

The positioning of disk member components in the sterile field provides several advantages. Specifically, medical personnel (e.g., a scrub nurse) may manipulate the disk member to connect the drape to the thermal treatment system without compromising sterility of personnel or the sterile field. Further, sensors for surgical drapes (e.g., electrodes to detect leaks as described in one or more of the aforementioned patents and/or patent application publications) may be placed beneath the disk member cover within the drape container to protect the sensor when medical personnel stir the sterile liquid within the thermal treatment system basin. Moreover, this placement may eliminate the need for a protective covering or sleeve for the sensor. The sleeve is typically utilized to prevent damage to the sensor during stirring of the sterile liquid and to inhibit false readings by the sensor when conductive items (e.g., stainless steel pitcher, etc.) are placed in the basin. However, the disk member cover may serve the function of the sleeve within the basin to protect the sensor from damage and to prevent placement of conductive items on the sensor.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
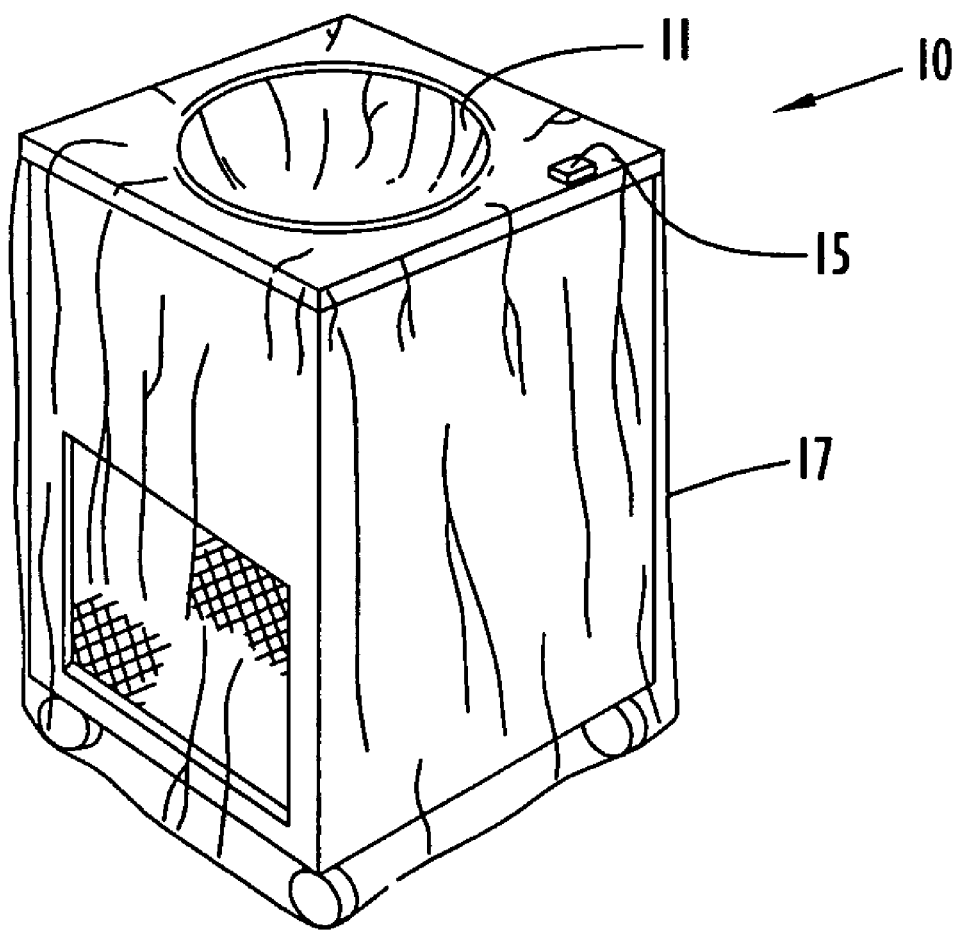
FIG. 1 is a view in perspective of an exemplary thermal treatment system employing a surgical drape according to the present invention.
Figure 4:
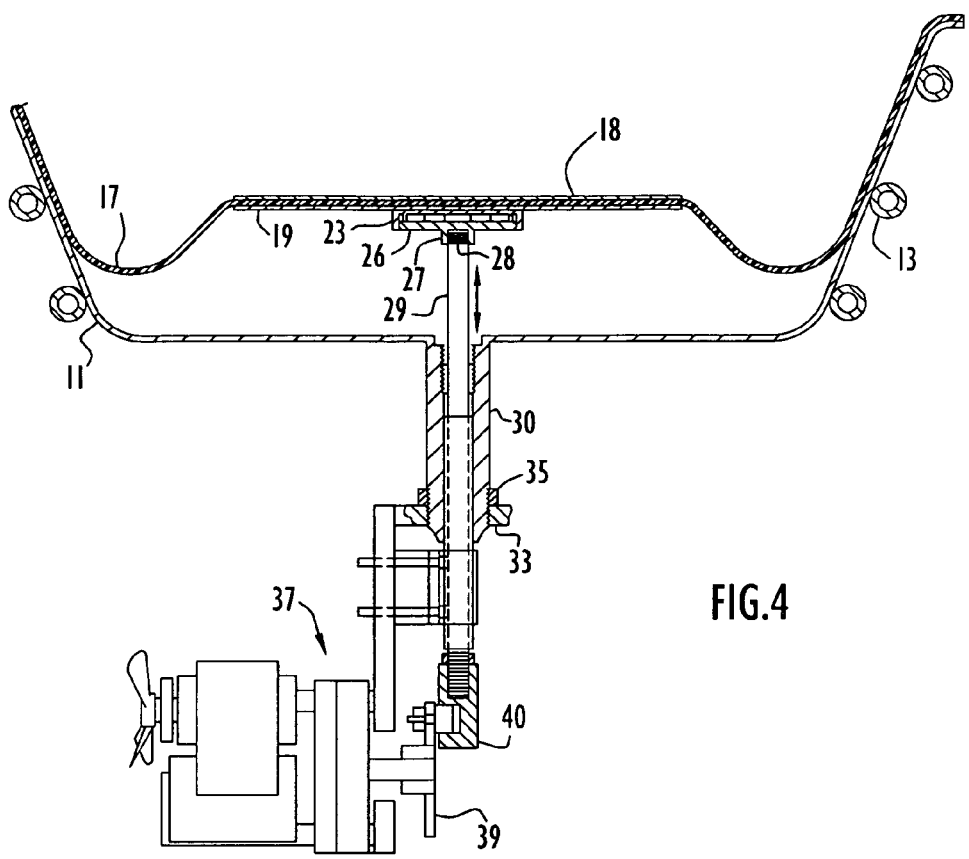
FIG. 4 is a view in elevation and partial section of the surgical drape of FIG. 2 secured to a dislodgment mechanism for manipulating the drape to dislodge congealed sterile medium adhered to drape container sides within a thermal treatment system basin.

An exemplary thermal treatment system employing a surgical drape according to the present invention is illustrated in FIG. 1. Specifically, the thermal treatment system is of the type described in one or more of the above-referenced U.S. patents and patent application publications (e.g., U.S. Pat. No. 5,331,820, etc.) and includes a cabinet 10 with a top surface having a basin 11 mounted thereon in an appropriately sized recess. Although shown rounded with a circular rim, basin 11 may be oval, rectangular, square or any desired shape. Basin 11 is made of thermally conductive material, typically stainless steel, and includes a generally flat circular bottom wall and, in the illustrated embodiment, a generally frusto-conical side wall. A conventional refrigeration unit is disposed within cabinet 10 (e.g., it being noted that only an evaporator 13 of that unit is shown in FIG. 4). The refrigeration unit typically includes a compressor, a condenser and an expansion control unit connected by appropriate fluid conduits in a closed refrigeration loop with evaporator 13. The evaporator is in the form of coil wound about the exterior surface of basin 11 in thermal transfer relation therewith. When the refrigeration unit is activated via appropriate controls 15 on the top surface of cabinet 10, evaporator 13 cools the side wall of basin 11 to a temperature substantially below the freezing temperature of sterile liquid disposed within the basin and used in forming surgical slush. This temperature is preferably on the order of –30° F. to 10° F. For further examples of the structure and operation of the refrigeration unit, reference is made to the aforementioned U.S. patents and patent application publications (e.g., U.S. Pat. Nos. 4,393,659 (Keyes et al.), 4,934,152 (Templeton), 5,331,820 (Faries, Jr. et al.), etc.).

A sterile drape 17, preferably transparent, is disposed over the top and hangs down along the sides of cabinet 10, and is made to conform to the side wall of basin 11. The portion of drape 17 disposed in the basin serves as a sterile receptacle or container for sterile liquid placed therein to be frozen to the desired sterile slush consistency. Typical sterile liquid used for this purpose is a 0.80% to 0.95% sodium chloride solution (i.e., saline). Slush produced by the thermal treatment system generally adheres to the sides of the drape container. In order to collect the slush formed within the drape container, the thermal treatment system includes a dislodgment mechanism to manipulate the drape and dislodge the slush adhered to the drape container sides. A disk or plate 19 (FIGS. 2-3) is secured to or in contact with the drape and is configured to generally match the contour of the basin bottom while being supported, in a manner described below, slightly above the basin bottom between the drape and the basin. The disk basically couples the drape to the dislodgment mechanism as described below.

Figure 2:
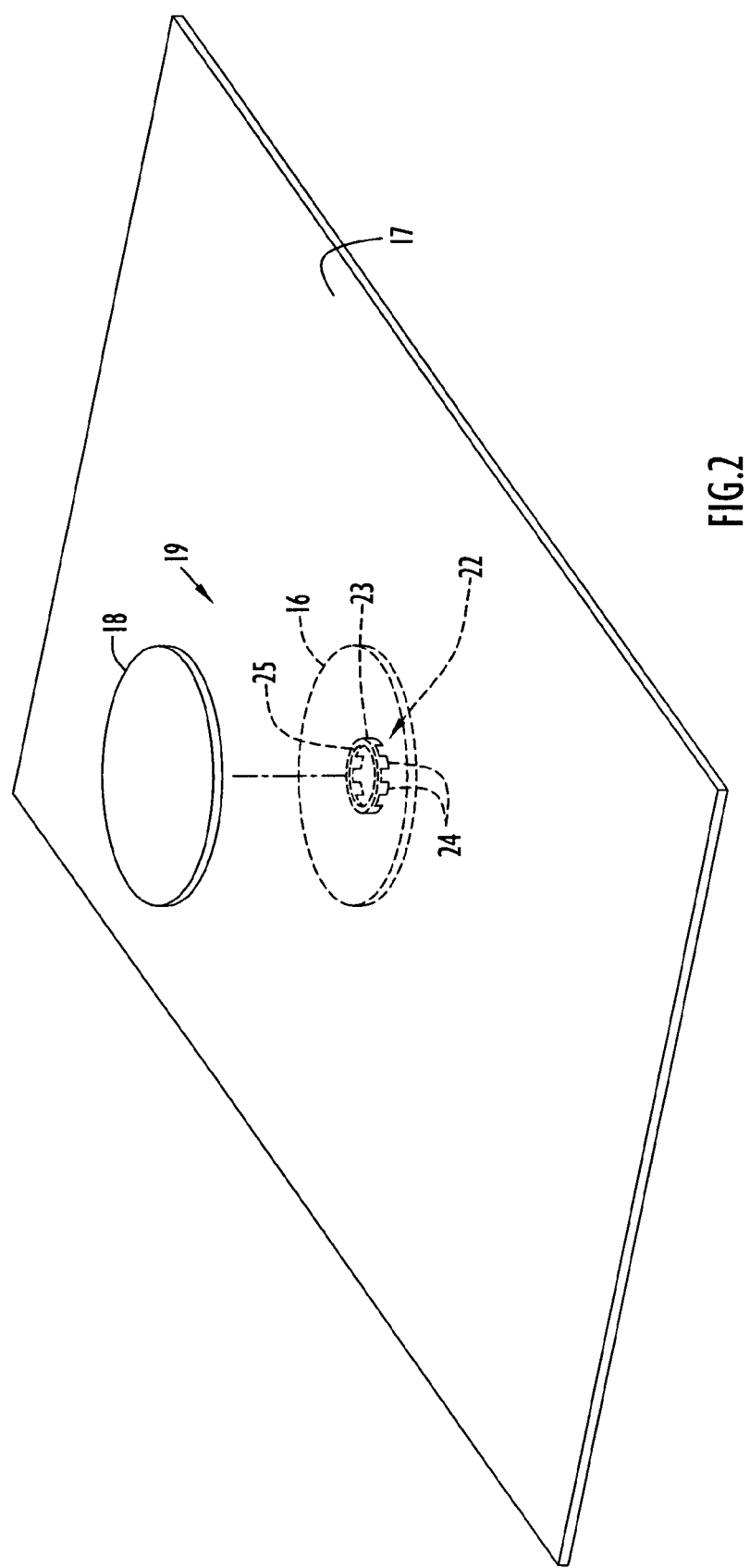
FIG. 2 is an exploded view in perspective of the surgical drape of FIG. 1.
Figure 3:
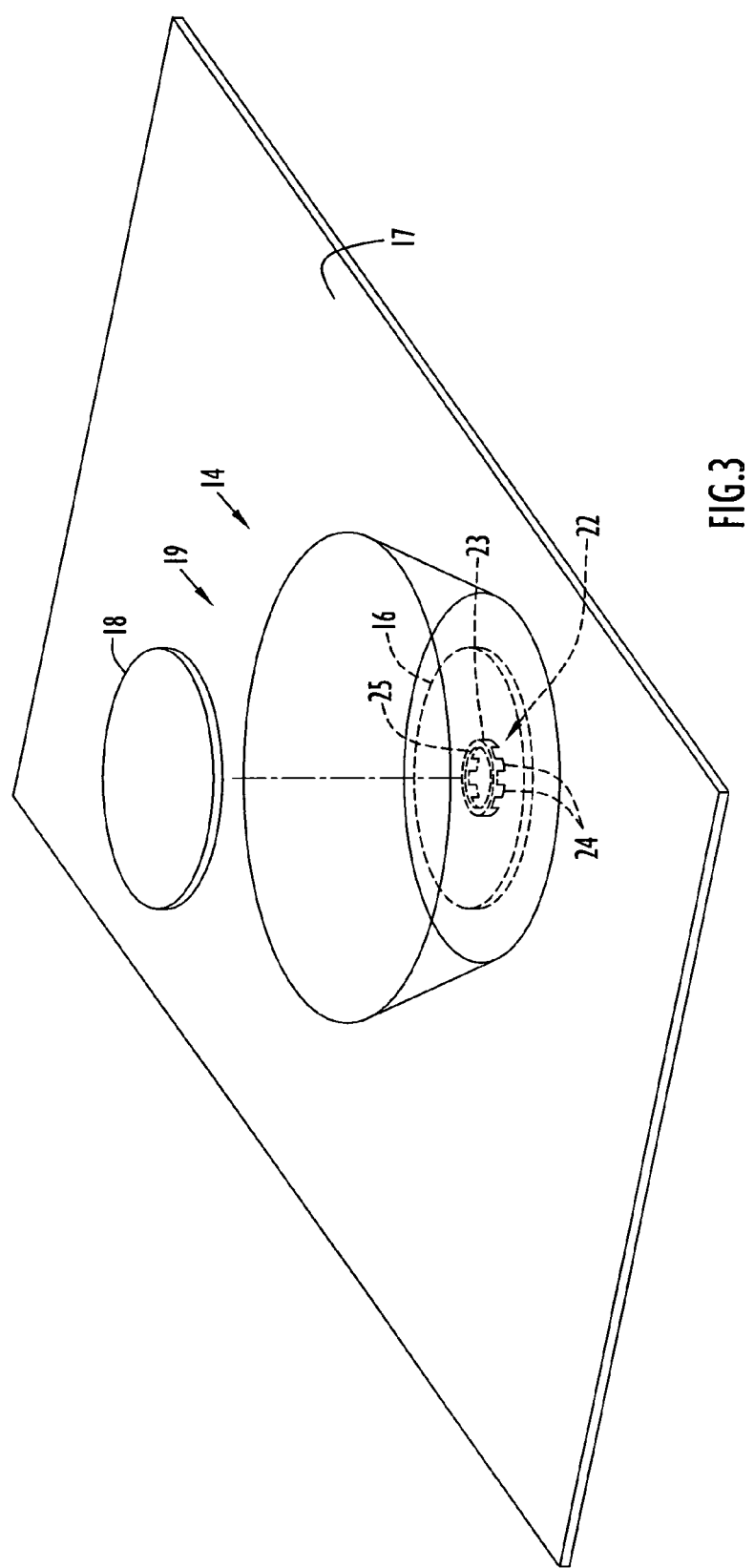
FIG. 3 is an exploded view in perspective of an alternative embodiment of the surgical drape of FIG. 2 including a preformed container portion according to the present invention.

Drape 17 is made from a material that is impervious to the sterile liquid and sufficiently soft and flexible to conform to the basin side wall (FIG. 2). The drape may also have a preformed section contoured to match the basin side wall as described below (FIG. 3). The thickness of the drape is preferably minimized to render thermal transfer therethrough most efficient, yet the thickness is sufficient to resist tearing and puncturing during normal use. Typically, and by way of example only, the drape may be made of materials commonly used in hospitals for drapes and has a thickness in the range of 3.0 to 10.0 mils, but may be of any thickness. The drape and corresponding adhered plate 19 are designed to be disposable after a single use (i.e., after a single surgical procedure) and are provided pre-sterilized and pre-packaged in a manner to preserve their sterile state during storage.

Referring to FIG. 2, disk or plate 19 is generally circular and includes a base 16 and a cover member 18. Base 16 is substantially circular and preferably has the base upper surface permanently secured to the underside or non-sterile surface of drape 17 via any conventional or other technique (e.g., adhesive, bonding, etc.). The base is typically centrally disposed on the drape, but may be disposed at any location on the drape for placement in a thermal treatment system basin (e.g., coincident the drape portion forming the drape container in the basin). The base is formed of a flexible material (e.g., plastic, drape material, etc.) and includes an engagement member 22 substantially centrally disposed on the base to engage the thermal treatment system dislodgment mechanism as described below. The engagement member is substantially annular and is preferably formed of a hard plastic material. The engagement member includes a series of teeth or projections 23 extending downward from a bottom surface of the engagement member proximate the member peripheral edge. The projections are angularly displaced from each other about the engagement member periphery in a generally uniform manner. The projections are substantially rectangular and each includes a short lip 24 extending radially inward from that projection. An annular wall 25 is spaced concentrically inward from projections 23 and likewise extends from the bottom surface of the engagement member. The annular wall is axially shorter than projections 23. The projections are sufficiently resilient to permit a substantially circular connector plate of the dislodgment mechanism to be received with a snap-fit engagement in the space between projections 23 and wall 25 as described below.

Cover 18 is substantially circular and preferably has the cover bottom surface facing and/or secured to the drape sterile surface to engage base 16. The cover may be secured to the base and/or drape via any conventional or other technique (e.g., adhesive, bonding, welding, snap-fit or other engagement, etc.). In other words, the cover attaches to the base with drape 17 disposed therebetween. Since the cover is placed in the sterile field, medical personnel may manipulate the cover to connect the drape to the thermal treatment system without compromising sterility of personnel or the sterile field. Further, sensors for surgical drapes (e.g., electrodes to detect leaks as described in one or more of the aforementioned patents and/or patent application publications) may be placed beneath the cover within the drape container to protect the sensor when medical personnel stir the sterile liquid in the basin as described below. Moreover, this placement may eliminate the need for a protective covering or sleeve for the sensor. The sleeve is typically utilized to prevent damage to the sensor from the stirring of the liquid and to inhibit false readings by the sensor when conductive items (e.g., stainless steel pitcher, etc.) are placed in the basin. However, the cover may serve the function of the sleeve to protect the sensor from damage and to prevent placement of conductive items on the sensor.

Drape 17 may alternatively include a preformed container portion as illustrated in FIG. 3. Specifically, drape 17 is substantially similar to the drape described above and includes a preformed section 14 contoured to match the basin side wall to form a drape receptacle or container for containing the sterile liquid within the thermal treatment system basin. The preformed section may be disposed at any suitable locations on the drape. The preformed container portion is typically thicker than the remaining portions of the drape in order to resist puncture and enable the container portion to maintain the shape of the basin. By way of example only, the container portion may be made of a heavy gauge polyethylene/ionomer resin blend having a thickness of approximately ten through sixteen mils, but may be of any thickness. The percentage of ionomer resin in the blend is in the approximate range of forty to seventy percent.

Disk or plate 19 is generally circular and includes base 16 and cover member 18, each as described above. Base 16 is substantially circular and preferably has the base upper surface permanently secured to the underside or non-sterile surface of the preformed section bottom wall via any conventional or other technique (e.g., adhesive, bonding, etc.). The base is typically centrally disposed on the bottom wall of preformed section 14, but may be disposed at any location on the preformed section. The base is formed of a flexible material (e.g., plastic, drape material, etc.) and includes generally annular engagement member 22, as described above, substantially centrally disposed on the base to engage the thermal treatment system dislodgment mechanism as described below.

The engagement member includes teeth or projections 23 and annular wall 25, each as described above. The projections extend downward from a bottom surface of the engagement member proximate the member peripheral edge and are angularly displaced from each other about the engagement member periphery in a generally uniform manner as described above. The projections are substantially rectangular and each includes short lip 24 extending radially inward from that projection as described above. Annular wall 25 is spaced concentrically inward from projections 23 and likewise extends from the bottom surface of the engagement member. The annular wall is axially shorter than projections 23, where the projections are sufficiently resilient to permit the circular connector plate of the dislodgment mechanism to be received with a snap-fit engagement in the space between projections 23 and wall 25 as described below.

Cover 18 is substantially circular and preferably has the cover bottom surface facing and/or secured to the sterile bottom surface of the preformed container portion to engage base 16. The cover may be secured to the base and/or drape via any conventional or other technique (e.g., adhesive, bonding, welding, snap-fit or other engagement, etc.). In other words, the cover attaches to the base with preformed section 14 of drape 17 disposed therebetween. This arrangement provides several advantages as discussed above.

Figure 5:
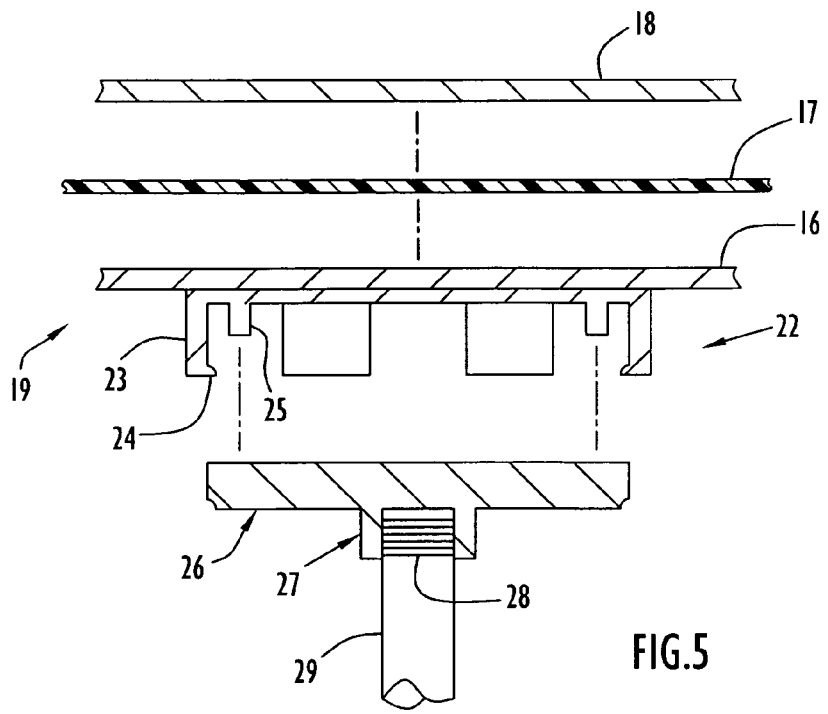
FIG. 5 is an exploded detailed view in partial section illustrating the manner in which the surgical drape of FIG. 2 is connected to the dislodgement mechanism of FIG. 4 according to the present invention.

The manner in which drape 17 engages the thermal treatment system is illustrated in FIGS. 4-5. By way of example only, FIGS. 4-5 illustrate a flat drape (FIG. 2) coupled to the thermal treatment system. However, drape 17 including preformed section 14 (FIG. 3) may be coupled to the thermal treatment system in substantially the same manner described below. Initially, cabinet 10 includes a dislodgment mechanism disposed therein to dislodge congealed sterile liquid adhered to the drape container or basin side wall. The mechanism includes a substantially circular connector plate 26 to engage disk 19 of the drape. The bottom of plate 26 is provided with a centrally located downwardly depending hollow cylindrical stem 27. Stem 27 is interiorly threaded to receive a threaded tip 28 of a shaft 29 extending upwardly through the bottom of basin 11. In particular, the bottom of basin 11 is provided with a central hole communicating with a bore in an adapter tube 30 secured at its upper end to the bottom of basin 11 by any conventional or other securing techniques. The bottom end of adapter tube 30 is externally threaded and is engaged by a support bracket 33 and a lock washer 35 such that bracket 33 is suspended interiorly of the machine cabinet (not shown in FIG. 4). A gear motor assembly, generally designated at 37, is supported by bracket 33 and includes a rotor 39 operatively engaged with a bearing track 40. Drive shaft 29 has its bottom end operatively engaged to bearing track 40 to cause the shaft to reciprocate longitudinally as rotor 39 rotates. Shaft 29 extends upwardly through adapter tube 30 and has its upper end secured to the center of the underside of plate 26 in the manner described above. Accordingly, as motor 37 reciprocates shaft 29 up and down, the shaft moves disk 19 up and down. The disk, in turn, moves the bottom of the drape container up and down to loosen pieces of frozen saline that form on the drape. The loosened pieces fall and collect in the center of the drape container as surgical slush.

Connector plate 26 has a diameter slightly smaller than the collective diameter formed by the inside surfaces of projections 23, but slightly larger than the collective diameter formed by the inner edges of lips 24. Accordingly, when disk 19 is properly centered in basin 11 and pushed axially downward onto plate 26, the plate resiliently forces lips 24 and projections 23 outward until the plate axially passes the lips and its flat upper surface is stopped by the bottom annular edge of inner annular wall 25. Once plate 26 clears lips 24, projections 23 and corresponding lips 24 resiliently return to their unstressed position with lips 24 extending a short radial distance along the bottom surface of the plate. The plate is thusly engaged in a snap fit by the disk.

For use in basins having shapes other than circular, it is to be understood that drape plate 19 would be configured correspondingly, and, further, that connector plate 26 and engagement member 22 are not constrained to circular or annular shapes, respectively, but need only interact to form a secure snap fit attachment between drape plate 19 and the dislodgment mechanism. Moreover, resilient projections 23 can be in the form of a continuous wall with a corresponding lip to form the snap fit between drape plate 19 and the perimeter of connector plate 26. Similarly, inner wall 25 can include a series of separated spaced wall increments to form an intermittent snap fit between drape plate 19 and connector plate 26. The projections and wall may be employed as a continuous wall or wall segments in any desired combination or fashion to provide a snap fit engagement between the connector plate and disk.

Drape 17 may be secured to the base and/or cover of disk 19 via a layer of an adhesive substance. The preferred adhesive is hot melt acrylic, although other adhesive materials may be utilized (e.g., cyanoacrylate, UV-cure acrylate, epoxy, urethane, silicon, etc.). The drape and disk may also be secured together by welding techniques (e.g., radiofrequency welding, hot plate welding, ultrasonic welding, etc.). The optimum adhesive or welding technique depends upon the materials employed for the drape and disk. Typical drape materials include polyurethane, polyvinylchloride, thermoplastic olefins, polyethylene, polypropylene, copolymers of propylene and polyethylene. Importantly, the drape material must be impervious to the sterile medium (e.g., saline) from which the sterile slush is formed. Disk 19 (e.g., base and cover) should be sufficiently rigid to support the pile of surgical slush without bending, flexing or breaking. Typically, the disk is approximately three-quarters inch thick and may be constructed of any suitable materials (e.g., polycarbonate, acronitrile-butadiene-styrene copolymer, polymethylmethacrylate, rigid polyvinylchloride, rigid polyurethane, nylon, polyethylene, polystyrene and other rigid thermoplastics capable of being machined, thermoformed or injection molded to the desired shape).

Operation of the drape with the exemplary thermal treatment system is described with reference to FIGS. 1-5. Initially, plate 26 is independently attached to drive shaft 29 by threadedly engaging shaft tip 28 in stem 27 at the underside of the plate. In many instances, plate 26 will already be secured to the drive shaft since the plate is located below the sterile field and need not be replaced for each procedure. Drape 17 (FIG. 2 or 3) is removed from its sterile package and positioned with the underside of disk 19 centered in basin 11 above plate 26. The disk is pushed downward until annular engagement member 22 snaps onto and engages plate 26. The drape is thereby properly positioned to form or place a drape container within the basin to be automatically manipulated by reciprocating drive shaft 29, whereby congealed sterile medium is automatically removed from the drape container sides.

When the surgical slush machine is operating, the sterile liquid in the drape container (e.g., the preformed section or the container formed by the flat drape) freezes in pieces on the side walls of that container which is cooled by evaporator 13 through basin 11. As disk 19 moves up and down, the drape (and/or preformed section) moves therewith, moving the drape container side walls relative to the basin walls. As the drape container side walls are displaced relative to the basin side walls, the solid pieces of frozen sterile medium dissociate from the drape container side wall and fall into the central area of the drape container where slush is collected.

Sensors for surgical drapes (e.g., electrodes to detect leaks as described in one or more of the aforementioned patents and/or patent application publications) may be placed beneath the cover within the drape container to protect the sensor when medical personnel stir sterile liquid in the basin. This placement may eliminate the need for a protective covering or sleeve for the sensor. The sleeve is typically utilized to prevent damage to the sensor from the stirring of the liquid and to inhibit false readings by the sensor when conductive items (e.g., stainless steel pitcher, etc.) are placed in the basin. However, the cover may serve the function of the sleeve to protect the sensor from damage and to prevent placement of conductive items on the sensor.

Figure 6:
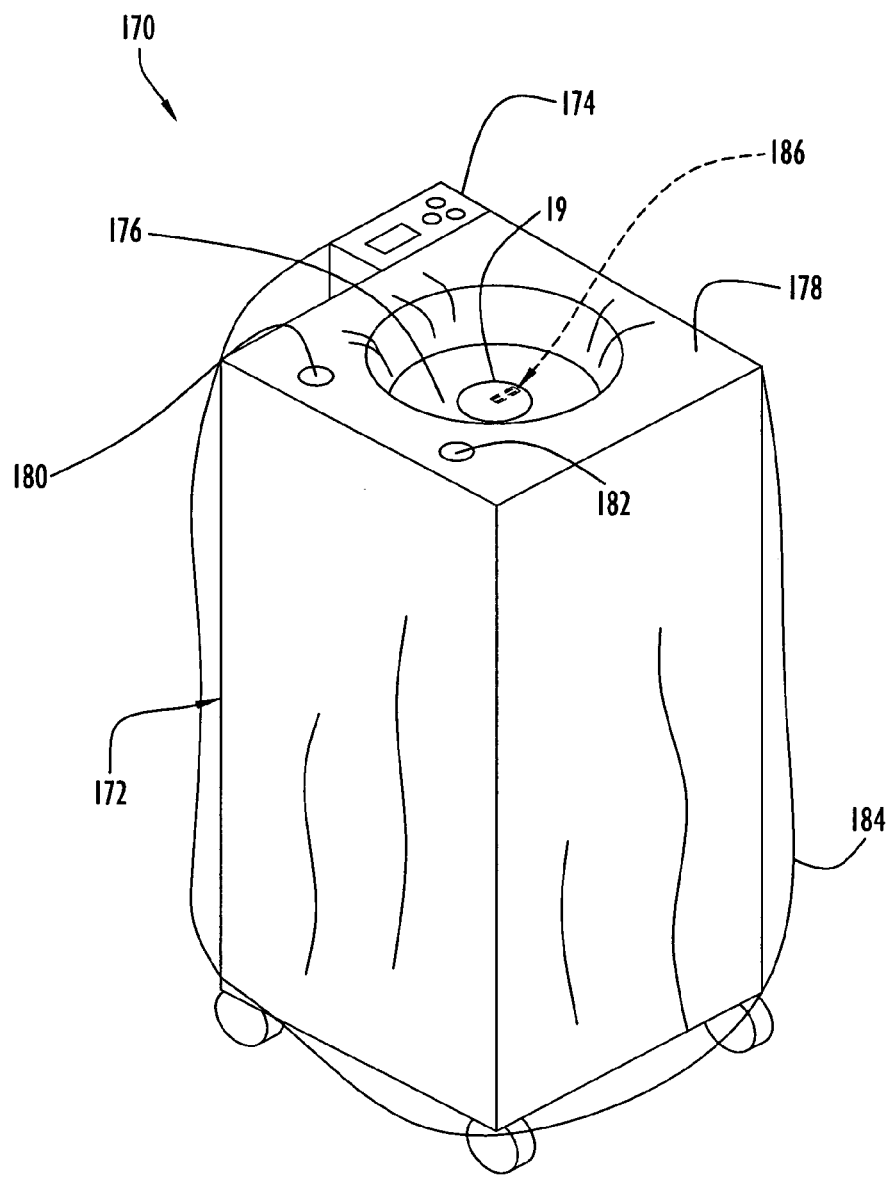
FIG. 6 is a view in perspective of an exemplary thermal treatment system employing a surgical drape including a sensor and a disk for engagement with a thermal treatment system dislodgment mechanism according to the present invention.

An exemplary thermal treatment system employing a drape with a sensor and disk is illustrated in FIG. 6. Initially, the thermal treatment system may be of the types of systems disclosed in the above-mentioned Faries, Jr. et al. patent documents (e.g., U.S. Pat. No. 6,810,881 and U.S. Patent Application Publication Nos. 2004/0200483, 2004/0200480, 2003/0231990 and 2003/0172937). Specifically, a thermal treatment system 170 to thermally treat a medical solution, and substantially similar to the system described above, includes a cabinet or housing 172, a wiring housing 174 attached to the cabinet and a cooling basin 176 recessed into a cabinet top surface 178. Basin 176 is substantially similar to basin 11 described above and may be of any shape, however, by way of example only, the basin is illustrated as being substantially circular. A cooler power switch 180 and a temperature controller/indicator 182 are provided on top surface 178 toward the cabinet front wall with the cooling basin residing between the power switch and controller. Wiring housing 174 is attached to the cabinet side wall that is closest to cooler power switch 180 and facilitates system connections as described below. A refrigeration system (not shown), substantially similar to the refrigeration system described above (e.g., evaporator, etc.), is disposed within the system cabinet to cool the sides of the basin and preferably congeal a sterile medium contained therein to form surgical slush. The refrigeration system is controlled by controller 182 in accordance with an entered desired temperature and temperatures measured by a temperature sensor (not shown). The system thermal devices are controlled in response to detection of solution and leaks within the drape container as described below. Further, the thermal treatment system includes a dislodgment mechanism substantially similar to the mechanism described above for FIG. 4 to manipulate the drape to collect surgical slush within the basin. In addition, the thermal treatment system may include a plurality of basins warming and/or cooling a sterile medium. Examples of cooling and/or plural basin systems are disclosed in the above-mentioned Faries, Jr. et al. patent documents.

A sterile drape 184, preferably transparent and substantially similar to drape 17 described above, is typically disposed over the top and sides of cabinet 172 and made to conform to the side wall and bottom of basin 176. Power switch 180 and controller 182 are disposed on top surface 178 of system cabinet 172 and are adjustable manually through drape 184. The portion of drape 184 disposed in basin 176 serves as a sterile container or receptacle for sterile liquid placed therein to be cooled. The drape includes disk or plate 19 to engage a thermal treatment system dislodgment mechanism (FIG. 7) as described below. In order to detect the presence of liquid and/or leaks within the drape container to maintain drape integrity and sterility of the sterile medium, drape 184 further includes a sensing device 186. Wiring housing 174 receives signals from the sensing device and includes wiring to transfer signals between that housing and detection circuitry within the thermal treatment system to control system operation in accordance with varying basin conditions (e.g., disable system operation in response to a leak or no solution within the basin, etc.). For further examples of the thermal treatment system, reference is made to the aforementioned Faries, Jr. et al. patent documents.

Figure 7:
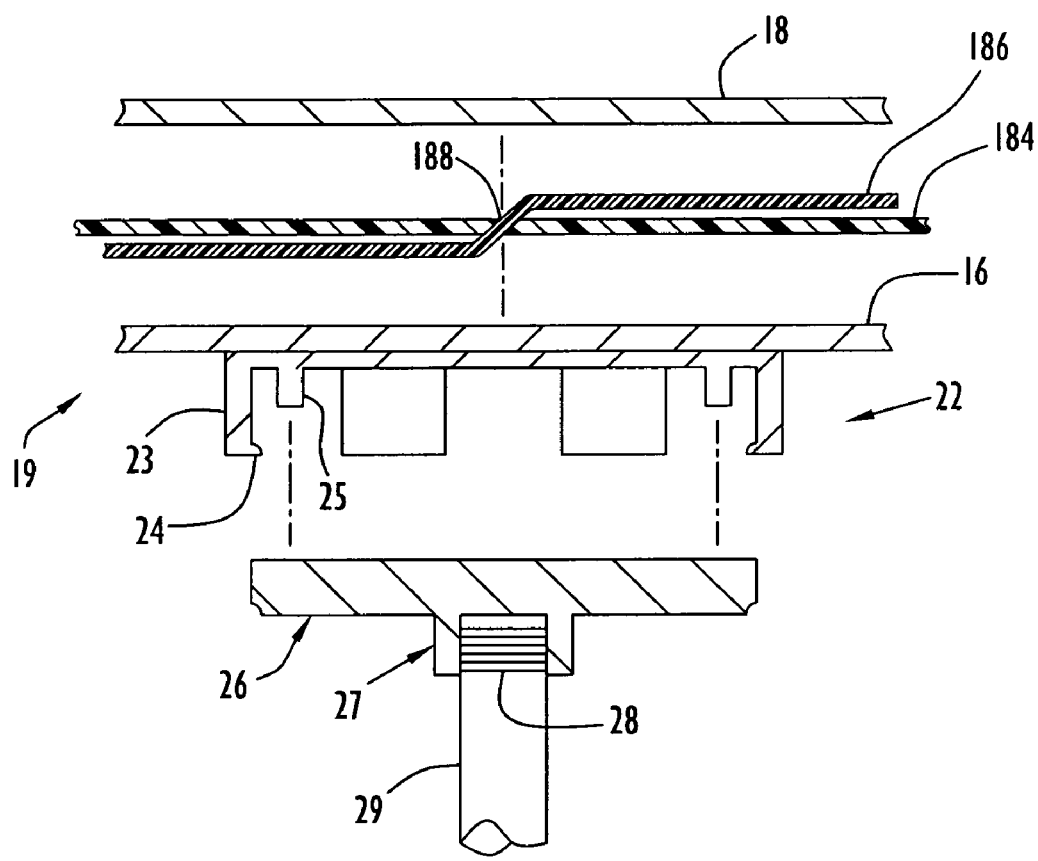
FIG. 7 is an exploded detailed view in partial section of the surgical drape of FIG. 6 connected to a dislodgement mechanism according to the present invention.

Referring to FIG. 7, disk or plate 19 is generally circular and includes base 16 and cover member 18, each as described above. Base 16 is substantially circular and preferably has the base upper surface permanently secured to the underside or non-sterile surface of drape 184 via any conventional or other technique (e.g., adhesive, bonding, etc.) as described above. The base is typically centrally disposed on the drape, but may be disposed at any location on the drape for placement in a thermal treatment system basin (e.g., coincident the drape portion forming the drape container in the basin). The base includes engagement member 22 substantially centrally disposed on the base to engage the thermal treatment system dislodgment mechanism as described above. The engagement member includes teeth or projections 23 and annular wall 25, each as described above. The projections extend downward from a bottom surface of the engagement member proximate the member peripheral edge and are angularly displaced from each other about the engagement member periphery in a generally uniform manner as described above. The projections are substantially rectangular and each includes short lip 24 extending radially inward from that projection as described above. Annular wall 25 is spaced concentrically inward from projections 23 and likewise extends from the bottom surface of the engagement member. The annular wall is axially shorter than projections 23, where the projections are sufficiently resilient to permit the circular connector plate of the dislodgment mechanism to be received with a snap-fit engagement in the space between projections 23 and wall 25 as described above.

Cover 18 is substantially circular and preferably has the cover bottom surface facing and/or secured to the drape sterile surface to engage base 16. The cover may be secured to the base and/or drape via any conventional or other technique (e.g., adhesive, bonding, welding, snap-fit or other engagement, etc.). In other words, the cover attaches to the base with drape 184 disposed therebetween.

Sensing device 186 is preferably in the form of a pair of electrodes and is disposed between cover 18 and base 16. The distal ends of the electrodes are attached to a plug or connector (not shown) that interfaces the wiring housing for conveyance of signals to the detection circuitry within the thermal treatment system. The electrodes pass through the drape from the sterile to the non-sterile drape sides via an opening or slit 188 defined in the drape. The electrode portion residing on the sterile drape side is disposed between the drape sterile surface and cover 18. The cover is secured to the base in a manner to protect the electrodes from medical personnel stirring or otherwise manipulating the sterile liquid or basin and/or to insulate the electrodes from conductive objects placed in the basin that may affect sensing device operation (e.g., conductive objects placed in the basin may cause the sensing device to provide false readings). The cover further enables the sterile liquid in the basin to contact the electrodes for detection of various conditions as described below. Since the sterile liquid may reside beneath cover 18, slit 188 is sealed to maintain the sterile field and prevent the sterile liquid from traversing the slit to the non-sterile drape side. The slit may be sealed via any conventional or other techniques, such as those disclosed in the aforementioned patent documents (e.g., one or more material segments attached to the drape sterile and/or non-sterile sides, etc.). Alternatively, the sensing device may be disposed on the drape at any locations and in any manner relative to the disk (e.g., the electrode portion residing on the sterile drape side may be disposed on the top surface of cover 18 to contact the sterile liquid, etc.).

The electrode portion residing on the non-sterile drape side extends beneath the drape and along the basin to wiring housing 174 to convey sensing device or electrode signals to the detection circuitry. In particular, the sensing device detects the presence of liquid and leaks within the drape container in response to current flow between the electrodes and ground (e.g., the basin beneath the drape) indicating various conditions. The current flow causes a respective change in voltage that is detected by the detection circuitry within the thermal treatment system (e.g., particular voltages correspond to drape container conditions). Wiring housing 174 receives signals from the electrodes and includes wiring to transfer signals between that housing and the detection circuitry to control system operation in accordance with the varying basin conditions (e.g., disable system operation in response to a leak or no solution within the basin, etc.). For further examples of the thermal treatment system, reference is made to the aforementioned Faries, Jr. et al. patent documents.

Drape 184 may include a pre-formed container portion and be secured to the base and/or cover of disk 19 via a layer of an adhesive substance or by welding techniques as described above. The drape along with disk 19 and sensing device 186 are designed to be disposable after a single use (i.e., after a single surgical procedure) and are provided pre-sterilized and pre-packaged in a manner to preserve their sterile state during storage.

Drape 184 is connected to the dislodgment mechanism in substantially the same manner described above for drape 17. In particular, connector plate 26 of the dislodgment mechanism has a diameter slightly smaller than the collective diameter formed by the inside surfaces of projections 23, but slightly larger than the collective diameter formed by the inner edges of lips 24. Accordingly, when disk 19 is properly centered in basin 176 (FIG. 6) and pushed axially downward onto plate 26, the plate resiliently forces lips 24 and projections 23 outward until the plate axially passes the lips and its flat upper surface is stopped by the bottom annular edge of inner annular wall 25. Once plate 26 clears lips 24, projections 23 and corresponding lips 24 resiliently return to their unstressed position with lips 24 extending a short radial distance along the bottom surface of the plate. The plate is thusly engaged in a snap fit by the disk.

Operation of the sensor drape with the exemplary thermal treatment system is described with reference to FIGS. 6-7. Initially, plate 26 is independently attached to the dislodgment mechanism or may already be secured to that mechanism since the plate is located below the sterile field and need not be replaced for each procedure. Drape 184 is removed from its sterile package and positioned with the underside of disk 19 centered in basin 176 above plate 26. The disk is pushed downward until annular engagement member 22 snaps onto and engages plate 26. The drape is thereby properly positioned to form or place a drape container within the basin to be automatically manipulated by reciprocating drive shaft 29 as described above, whereby congealed sterile medium is automatically removed from the drape container sides. Sensing device 186 is coupled to wiring housing 174 to convey detection signals to the detection circuitry as described above.

When the surgical slush machine is operating, the sterile liquid in the drape container (e.g., the preformed section or the container formed by the flat drape) freezes in pieces on the side walls of that container which is cooled by the refrigeration system through basin 176. As disk 19 moves up and down, the drape (and/or preformed section) moves therewith, moving the drape container side walls relative to the basin walls. As the drape side walls are displaced relative to the basin side walls, the solid pieces of frozen sterile medium dissociate from the drape side wall and fall into the central area of the drape container where slush is collected.

Sensing device 186 senses various basin conditions in accordance with contact between the sensing device electrodes and the sterile liquid as described above. The sensing device signals are relayed to wiring housing 174 for conveyance to the detection circuitry for processing. The detection circuitry controls system operation in accordance with the detected conditions as described above (e.g., disable system operation in response to a leak or no solution within the basin, etc.).

It will be appreciated that the embodiments described above and illustrated in the drawings represent only a few of the many ways of implementing a surgical disk drape and method of dislodging surgical slush within thermal treatment system basins.

The drapes may be of any size, shape or thickness, and may be constructed of any suitable materials. The drapes are preferably transparent or translucent to facilitate manipulation of controls through the drape, however, the drapes may have any degree of transparency (e.g., including opaque). The drapes may be manipulated in any fashion with any portions of the drapes serving as a drape receptacle within a corresponding basin. The drapes may be of sufficient size to accommodate and form drape receptacles within any quantity of thermal treatment system basins.

The drapes may include any quantity of preformed sections of any shape, size or thickness, constructed of any suitable materials and disposed at any suitable locations. The drapes may be utilized to thermally treat (e.g., heat, cool, freeze, etc.) any desired medical items or solutions (e.g., saline, drugs, instruments, containers, etc.).

The drapes may include any quantity of disks disposed at any suitable locations. The disk may be of any shape or size and may be constructed of any suitable materials. The base may be of any quantity, shape or size, may be disposed at any locations on the drape and may be constructed of any suitable materials. The base may be secured to the drape via any conventional or other techniques. The engagement member may be of any quantity, shape or size, may be disposed at any locations on the base and may be constructed of any suitable materials. The engagement member may include any quantity of projections of any shape or size and disposed at any locations on the engagement member in any fashion. The projections may be constructed of any suitable materials and may include any quantity of lips or other protrusions of any shape or size disposed and/or oriented in any fashion to engage the dislodgment mechanism. The engagement member inner wall may be of any quantity, shape or size, may be disposed at any location and may be constructed of any suitable materials. The projections and inner wall may be in the form of a continuous wall or a series of wall increments in any desired combination. The engagement member may be attached to the base via any conventional or other techniques (e.g., adhesives, welding, formed integral, etc.). Similarly, the projections and wall may be attached to the engagement member via any conventional or other techniques (e.g., adhesives, welding, formed integral, etc.). The engagement member may be configured in any manner (e.g., fastener, magnetic, interlocking components, etc.) to engage the dislodgment mechanism.

The cover may be of any quantity, shape or size, may be disposed at any locations on the drape and may be constructed of any suitable materials. The cover may be attached to the drape and/or base via any conventional or other techniques. The disk may be arranged relative to the drape in any fashion. For example, the entire disk may be disposed on the sterile drape surface or in the sterile field and engage the dislodgment mechanism through the drape. Alternatively, the engagement member may be disposed on the drape non-sterile surface and be attached through the drape to the remaining portions of the disk disposed on the drape sterile surface. Any portion of the disk may be disposed on the sterile and/or non-sterile drape surfaces in any fashion.

The disk may be configured to engage any portion of the dislodgment mechanism. Further, the disk may be configured to cover, protect or keep apart any items within the drape container. The drape may include any special features (e.g., sensors, materials, securing mechanisms, etc.), such as those described in the aforementioned patents and patent application publications. The thermal treatment systems may be implemented by any system thermally treating (e.g., heating and/or cooling) a sterile medium or other medical item, such as the types disclosed in the aforementioned patents and patent application publications. The systems may include any quantity of cooling and/or heating basins of any shape or size and disposed at any locations. The drapes may be configured with a sufficient quantity of disks, preformed sections and/or sensing devices to form drape receptacles in each basin and function in substantially the same manner described above. The thermal treatment systems may employ any quantity of any type of thermal device to heat and/or cool the sterile medium or other items (e.g., coils, heaters, refrigeration components, thermoelectric devices, etc.). The thermal treatment systems may include any quantity of any type of dislodgment mechanism for use with the drapes, such as the types disclosed in the aforementioned patents and patent application publications.

The base and cover may include any mated or other configurations to be removably or permanently attached to each other to form the disk. For example, the base and cover may be flat and bonded to opposing drape surfaces. Alternatively, the base and/or cover may be in the form of a dish (e.g., circular or other shape) with a peripheral wall, where the dimensions of one are sufficient to be disposed within the confines of the other with the drape disposed therebetween. Further, the base and/or cover may include securing or fastening devices to enable removable or permanent attachment of the base to the cover.

The engagement member may include any configuration to secure or maintain the drape on the dislodgment mechanism (e.g., friction fit, snap-fit, etc.). For example, the engagement member may include securing or fastening devices to engage the dislodgment mechanism. Alternatively, the engagement member or base may include a receptacle or open area (e.g., defined by a peripheral wall or other configuration) to receive the dislodgment mechanism connector plate or other component for a friction fit, snap-fit or other type of engagement, or to receive the dislodgment mechanism connector plate or other component, where the weight of the engagement member, disk (e.g., base and/or cover) and/or sterile medium placed in the drape container presses the disk down onto or maintains the disk position on the dislodgment mechanism.

The disk may be permanently or removably secured to the drapes at any location via any conventional or other securing techniques (e.g., welding, bonding, adhesives, formed integral with the drape, fasteners, etc.). Alternatively, the disk may be coupled to the dislodgment mechanism with the drapes (or preformed container) placed over the disk. The disk may manipulate the drape container as described above. For example, a drape (e.g., flat or with a preformed container portion) may be placed over the disk (e.g., with or without being secured to the disk) or may be placed over another drape including a disk secured to that other drape (e.g., with or without being secured to the other drape or disk).

The sensing device may include any quantity of electrodes or electrode strips and may be disposed at any suitable locations on the drape. The electrodes may be constructed of any suitable conductive materials. The electrodes may be of any shape or size, and may be fastened to the drape or disk at any suitable locations and in any manner relative to the disk (e.g., above, below or between the cover and base, etc.) via any conventional or other fastening techniques. The drape opening may be of any quantity, shape or size and may be defined in the drape at any suitable locations. The drape opening may be sealed via any conventional or other techniques (e.g., patches of any quantity, shape, size or materials disposed at any suitable locations on the sterile and/or non sterile drape surfaces, etc.). The drape may include any quantity of sensing devices for a corresponding basin where the sensing device signals may be combined in any fashion (e.g., at least one device detecting liquid, combined logically (e.g., AND, OR, etc.), etc.) to determine occurrence of drape container conditions (e.g., solution or leaks present). The sensing device may alternatively include any conventional or other sensing devices to detect conditions (e.g., liquid sensor, liquid level sensor, pressure or weight sensor, conductive members, etc.). The drapes may include any quantity of disks and/or or sensing devices either individually or in any combinations.

It is to be understood that the terms "top", "bottom", "front", "rear", "side", "height", "length", "width", "upper", "lower" and the like are used herein merely to describe points of reference and do not limit the present invention to any particular orientation or configuration.

The drapes are not limited to the applications or systems described above, but may be utilized to facilitate dislodgment of any types of items from the drape.

From the foregoing description, it will be appreciated that the invention makes available a novel surgical disk drape and method of dislodging surgical slush within thermal treatment system basins, wherein a surgical drape for a thermal treatment system basin includes a disk disposed within a drape sterile field for attachment to a system dislodgment mechanism.

Having described preferred embodiments of a new and improved surgical disk drape and method of dislodging surgical slush within thermal treatment system basins, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical drape assembly for use as a sterile container of sterile medium in a surgical slush machine including a cooled basin recessed in the top surface of the machine and a dislodgment mechanism to manipulate said drape assembly to collect surgical slush, said drape assembly comprising:
   a conformable sheet of sufficient size to cover and hang down from the top surface of said machine to maintain a sterile field above said machine, wherein said sheet includes sterile and non-sterile surfaces; and
   a plate member secured to said sheet to engage said dislodgment mechanism and including:
      a cover member disposed on a first sterile surface of said sheet and including a top surface and a bottom surface underlying said top surface and formed of peripheral and interior portions, wherein said peripheral portions of said bottom surface are disposed toward and include a cover member periphery and said interior portions encompass remaining portions of said bottom surface and are disposed inward of said peripheral portions within a cover member interior, wherein said peripheral and interior portions of said bottom surface are each engageable by said sterile surface of said sheet, and wherein at least an interior portion of said bottom surface engages said sterile surface of said sheet; and
      a base member disposed on an opposing non-sterile sheet surface to engage said dislodgment mechanism.

2. The drape assembly of claim 1, further including at least one sensor disposed on said sheet to detect conditions within said sterile container.

3. A surgical drape assembly for use as a sterile container of sterile medium in a surgical slush machine including a cooled basin recessed in the top surface of the machine and a dislodgment mechanism to manipulate said drape assembly to collect surgical slush, said drape assembly comprising:
   a sterile conformable sheet of sufficient size to cover and hang down from the top surface of said machine to maintain a sterile field above said machine;
   a plate member secured to said sheet to engage said dislodgment mechanism and including:
      a cover member disposed an a first surface of said sheet; and
      a base member disposed on an opposing sheet surface to engage said dislodgment mechanism; and
   at least one sensor disposed between said base member and said cover member.

4. A surgical drape assembly for use as a sterile container of sterile medium in a surgical slush machine including a cooled basin recessed in the top surface of the machine and a dislodgment mechanism to manipulate said drape assembly to collect surgical slush, said drape assembly comprising:
   a sterile conformable sheet of sufficient size to cover and hang down from the top surface of said machine to maintain a sterile field above said machine;
   a plate member secured to said sheet to engage said dislodgment mechanism and including:
      a cover member disposed on a first surface of said sheet; and
      a base member disposed on an opposing sheet surface to engage said dislodgment mechanism; and
   at least one sensor disposed on said sheet to detect conditions within said sterile container, wherein at least one sensor includes a plurality of electrodes to measure current flow therebetween indicating said conditions within said sterile container.

5. The drape assembly of claim 1, wherein said sheet includes a pre-formed container portion adapted to be substantially conformed to said basin.

6. The drape assembly of claim 1, wherein said base member includes an engagement member to engage said dislodgment mechanism in at least one of a friction fit, snap-fit and weight-based type of engagement.

7. The drape assembly of claim 6, wherein said engagement member includes:
   a plurality of resilient projections extending from an engagement member periphery, wherein each projection includes a lip extending transversely therefrom; and
   a wall radially displaced from said projections to form a gap therebetween to receive and engage said dislodgment mechanism.

8. A surgical drape assembly for use as a sterile container of sterile medium in a surgical slush machine including a cooled basin recessed in the top surface of the machine and a dislodgment mechanism to manipulate said drape assembly to collect surgical slush, said drape assembly comprising:
   a sterile conformable sheet of sufficient size to cover and hang down from the top surface of said machine to maintain a sterile field above said machine;
   a plate member secured to said sheet to engage said dislodgment mechanism; and
   at least one sensor disposed on said sheet to detect conditions within said sterile container, wherein at least one sensor is disposed between said sheet and said plate member.

9. A surgical drape assembly for use as a sterile container of sterile medium in a surgical slush machine including a cooled basin recessed in the top surface of the machine and a dislodgment mechanism to manipulate said drape assembly to collect surgical slush, said drape assembly comprising:
- a sterile conformable sheet of sufficient size to cover and hang down from the top surface of said machine to maintain a sterile field above said machine;
- a plate member secured to said sheet to engage said dislodgment mechanism; and
- at least one sensor disposed on said sheet to detect conditions within said sterile container, wherein at least one sensor includes a plurality of electrodes to measure current flow therebetween indicating said conditions within said sterile container.

10. The drape assembly of claim 8, wherein said sheet includes a pre-formed container portion adapted to be substantially conformed to said basin.

11. The drape assembly of claim 8, wherein said plate member includes an engagement member to engage said dislodgment mechanism in at least one of a friction fit, snap-fit and weight-based type of engagement.

12. A thermal treatment system for thermally treating a sterile medium comprising:
- a system housing including a top surface;
- a basin recessed in said top surface for transferring thermal energy to said sterile medium;
- a drape covering and hanging down from said top surface of said housing with a portion of said drape disposed in said basin to form a drape container for collecting said sterile medium, wherein said drape includes sterile and non-sterile surfaces;
- a dislodgment mechanism to manipulate said drape container to collect surgical slush, wherein said drape includes a plate member to engage said dislodgment mechanism, said plate member including:
  - a cover member disposed on a first sterile drape surface and including a top surface and a bottom surface underlying said top surface and formed of peripheral and interior portions, wherein said peripheral portions of said bottom surface are disposed toward and include a cover member periphery and said interior portions encompass remaining portions of said bottom surface and are disposed inward of said peripheral portions within a cover member interior, wherein said peripheral and interior portions of said bottom surface are each engageable by said sterile surface of said drape, and wherein at least an interior portion of said bottom surface engages said sterile surface of said drape; and
  - a base member disposed on an opposing non-sterile drape surface to engage said dislodgment mechanism; and
- a thermal treatment unit in thermal relation with said basin for thermally treating said sterile medium.

13. A thermal treatment system for thermally treating a sterile medium comprising:
- a system housing including a top surface;
- a basin recessed in said top surface for transferring thermal energy to said sterile medium;
- a drape covering and hanging down from said top surface of said housing with a portion of said drape disposed in said basin to form a drape container for collecting said sterile medium, wherein said drape includes sterile and non-sterile surfaces and at least one sensor disposed within said basin to detect conditions within said drape container;
- a dislodgment mechanism to manipulate said drape container to collect surgical slush, wherein said drape further includes a plate member secured to said sterile and non-sterile drape surfaces and configured to engage said dislodgment mechanism, and wherein said at least one sensor is disposed between said drape and said plate member; and
- a thermal treatment unit in thermal relation with said basin for thermally treating said sterile medium.

14. A method of collecting surgical slush in a surgical slush machine including a cooled basin recessed in the top surface of the machine, a surgical drape assembly for use as a sterile container in said basin for a sterile medium and a dislodgment mechanism to manipulate said drape assembly to collect said surgical slush, said method comprising:
(a) engaging said dislodgment mechanism with said drape assembly via a plate member of said drape assembly to enable manipulation of said drape assembly and collection of said surgical slush within said sterile container, wherein said drape assembly includes sterile and non-sterile surfaces and said plate member includes:
- a cover member disposed on a first sterile drape assembly surface and including a top surface and a bottom surface underlying said top surface and formed of peripheral and interior portions, wherein said peripheral portions of said bottom surface are disposed toward and include a cover member periphery and said interior portions encompass remaining portions of said bottom surface and are disposed inward of said peripheral portions within a cover member interior, wherein said peripheral and interior portions of said bottom surface are each engageable by said sterile surface of said drape assembly, and wherein at least an interior portion of said bottom surface engages said sterile surface of said drape assembly; and
- a base member disposed on an opposing non-sterile drape assembly surface to engage said dislodgment mechanism.

15. The method of claim 14, wherein step (a) further includes:
(a.1) detecting conditions within said sterile container via at least one sensor disposed on said drape assembly.

16. A method of collecting surgical slush in a surgical slush machine including a cooled basin recessed in the top surface of the machine, a surgical drape assembly for use as a sterile container in said basin for a sterile medium and a dislodgment mechanism to manipulate said drape assembly to collect said surgical slush, said method comprising:
(a) engaging said dislodgment mechanism with said drape assembly via a plate member of said drape assembly to enable manipulation of said drape assembly and collection of said surgical slush within said sterile container, wherein said plate member includes a cover member disposed on a first drape assembly surface and a base member disposed on an opposing drape assembly surface to engage said dislodgment mechanism, wherein step (a) further includes:
(a.1) detecting conditions within said sterile container via at least one sensor, including a plurality of electrodes, disposed on said drape assembly, and measuring current flow between said electrodes indicating said conditions within said sterile container.

17. The method of claim 14, wherein said drape assembly includes a pre-formed container portion adapted to be substantially conformed to said basin to serve as said sterile container.

18. The method of claim 14, wherein step (a) further includes:

(a.1) engaging said dislodgment mechanism with said plate member in at least one of a friction fit, snap-fit and weight-based type of engagement.

19. A method of collecting surgical slush in a surgical slush machine including a cooled basin recessed in the top surface of the machine, a surgical drape assembly for use as a sterile container in said basin for a sterile medium and including sterile and non-sterile surfaces and at least one sensor to detect conditions within said sterile container, and a dislodgment mechanism to manipulate said drape assembly to collect said surgical slush, said method comprising:
(a) engaging said dislodgment mechanism with said drape assembly via a plate member of said drape assembly secured to said sterile and non-sterile surfaces and configured to engage said dislodgment mechanism to enable manipulation of said drape assembly and collection of said surgical slush within said sterile container; and
(b) detecting conditions within said sterile container via said at least one sensor, wherein said at least one sensor is disposed between said drape assembly sterile surface and said plate member.

20. A method of collecting surgical slush in a surgical slush machine including a cooled basin recessed in the top surface of the machine, a surgical drape assembly for use as a sterile container in said basin for a sterile medium and including at least one sensor to detect conditions within said sterile container, and a dislodgment mechanism to manipulate said drape assembly to collect said surgical slush, said method comprising:
(a) engaging said dislodgment mechanism with said drape assembly via a plate member of said drape assembly to enable manipulation of said drape assembly and collection of said surgical slush within said sterile container; and
(b) detecting conditions within said sterile container via said at least one sensor, wherein at least one sensor includes a plurality of electrodes, and step (b) further includes:
(b.1) measuring current flow between said electrodes indicating said conditions within said sterile container.

21. The method of claim 19, wherein said drape assembly includes a pre-formed container portion adapted to be substantially conformed to said basin to serve as said sterile container.

22. The method of claim 19, wherein step (a) further includes:
(a.1) engaging said dislodgment mechanism with said plate member in at least one of a friction fit, snap-fit and weight-based type of engagement.

23. A surgical drape assembly for use as a sterile container of sterile medium in a surgical slush machine including a cooled basin recessed in the top surface of the machine and a dislodgment mechanism to manipulate said drape assembly to collect surgical slush, said drape assembly comprising:
a conformable sheet of sufficient size to cover and hang down from the top surface of said machine to maintain a sterile field above said machine, wherein said sheet includes sterile and non-sterile surfaces; and
a plate member configured to engage said dislodgment mechanism and secured to one of said sheet sterile surface and a combination of said sheet sterile and non-sterile surfaces, wherein a plate member surface facing said sheet sterile surface includes peripheral and interior portions, wherein said peripheral portions of said facing surface are disposed toward and include a plate member periphery and said interior portions encompass remaining portions of said facing surface and are disposed inward of said peripheral portions within a plate member interior, wherein said peripheral and interior portions of said facing surface are each engageable by said sterile surface of said sheet, and wherein at least an interior portion of said facing surface engages said sterile surface of said sheet.

24. A method of collecting surgical slush in a surgical slush machine including a cooled basin recessed in the top surface of the machine, a surgical drape assembly for use as a sterile container in said basin for a sterile medium and a dislodgment mechanism to manipulate said drape assembly to collect said surgical slush, said method comprising:
(a) engaging said dislodgment mechanism with said drape assembly via a plate member of said drape assembly to enable manipulation of said drape assembly and collection of said surgical slush within said sterile container, wherein said drape assembly includes sterile and non-sterile surfaces and said plate member is configured to engage said dislodgment mechanism and is secured to one of said sterile surface and a combination of said sterile and non-sterile surfaces, wherein a plate member surface facing said drape assembly sterile surface includes peripheral and interior portions, wherein said peripheral portions of said facing surface are disposed toward and include a plate member periphery and said interior portions encompass remaining portions of said facing surface and are disposed inward of said peripheral portions within a plate member interior, wherein said peripheral and interior portions of said facing surface are each engageable by said drape assembly sterile surface, and wherein at least an interior portion of said facing surface engages said sterile surface of said drape assembly.

* * * * *